United States Patent
Yaar (12)

(10) Patent No.: US 6,366,806 B1
(45) Date of Patent: Apr. 2, 2002

(54) EMG ASSISTANT: A METHOD FOR THE AUTOMATED LOCALIZATION OF ROOT/ PLEXUS/NERVE/BRANCH-DAMAGE, USING THE ROUTINE CLINICAL (NEEDLE) ELECTROMYOGRAPHIC STUDY RESULTS

(75) Inventor: Israel Yaar, 53 Lantern La., Sharon, MA (US) 02067

(73) Assignee: Israel Yaar, Sharon, MA (US)

( * ) Notice: Subject to any disclaimer, the term of this patent is extended or adjusted under 35 U.S.C. 154(b) by 0 days.

(21) Appl. No.: 09/531,091

(22) Filed: Mar. 18, 2000

(51) Int. Cl.$^7$ ................................................ A61B 5/04
(52) U.S. Cl. ...................................................... 600/546
(58) Field of Search ................................. 600/546, 595, 600/587, 300, 301; 607/143; 128/897, 898

(56) References Cited

U.S. PATENT DOCUMENTS 5,052,406 A  * 10/1991  Nashner ...................... 600/595
5,284,154 A  *  2/1994  Raymond et al. ........... 600/554
5,551,445 A  *  9/1996  Nashner ...................... 600/595

* cited by examiner

Primary Examiner—Robert L. Nasser
Assistant Examiner—Brian Szmal (57) ABSTRACT

A novel computerized method for automatic diagnosis of clinical electromyographic (EMG) studies is presented. The elecromyographer (EMGer) performs a routine EMG study and assigns graded levels of pathology to each of the muscles examine. This data is input into the program. A priori, the program computes all the possible combinations (sets) of nerve damage, translates them to all possible combinations (sets) of muscle damage. Once the data is input, the program checks the input against all these muscle-sets for goodness of fit. Once the muscle-sets that best fit the EMGer's input are found, they are translated to the nerve-sets that produced them. Among the latter, only the nerve-sets that include the minimum number of damaged nerve-segments are retained and output as the best explanation for the EMGer's findings—the diagnosis.

1 Claim, 2 Drawing Sheets

EMG ASSISTANT: A METHOD FOR THE AUTOMATED LOCALIZATION OF ROOT/PLEXUS/NERVE/BRANCH-DAMAGE, USING THE ROUTINE CLINICAL (NEEDLE) ELECTROMYOGRAPHIC STUDY RESULTS

BACKGROUND OF THE INVENTION (1) Field of the Invention

This invention relates to medical diagnostic devices and methods and in particular to the electromyographical diagnosis of nerve damage.

(2) Description of the Related Art

Electromyography, as used clinically to diagnose nerve and muscle disorders, involves recording electrical signals (the electromyogram or EMG) from muscles by means of needle electrodes. These signals may be interpreted as normal or as abnormal for each muscle. The abnormal muscles are also graded for their level of abnormality. Usually, many muscles are sampled in order to make a comprehensive diagnosis. The EMG abnormalities may indicate muscle specific disease and nerve specific disease. In the latter, it may indicate a general (diffuse) disorder and focal or multi-focal disorders. The proposed method, henceforth called the EMGAssistant is dedicated to the latter two.

The interpretation of an EMG study as it pertains to the localization of root/plexus/nerve/branch-damage—or, in generality, nerve-segment damage—is an important part of the neurophysiological evaluation of patients. The current practice is based on established nerve-to-muscle wiring tables* and the slow, thinking-it-through, mental reasoning-process on the part of the physician (electromyographer or EMGer). As such, the current practice is far from perfect. It relies heavily on the individual physician capability to memorize complicated wiring tables, the physician's deducing capabilities and the time allocated to the task. This is especially true when the nerve damage involves more than one segment of one nerve, and/or when there are extraneous abnormalities on the EMG study that do not relate to the nerve damage at hand. These situations can confuse even the best electromyographer and render his diagnosis worthless. This situation is corrected by the EMGAssistant that makes the diagnostic process completely objective, precise, fast and with the ability of checking all possible answers.

*REFERENCES

Nerve-to-Muscle Wiring: This program uses the Peripheral Nervous System Nerve-to-Muscle Wiring Tables 1 & 2 to translate combinations of nerve-segment damage to muscle abnormalities and vice versa. These Nerve-to-Muscle Wiring tables are an educated compromise of many sources:

1. Medical Research Council, Memorandum No. 45: Aids to the examination of the peripheral nervous system, Crown, London, 1976.
2. E F Delagi and A O Perotto: Anatomic Guide for the Electromyographer, C C Thomas, Springfield, Ill. 1980.
2. R K Sethi and L L Thompson: The Electromyographer's handbook, Little, Brown and company, Boston, 1989.
4. J Kimura: Electrodiagnosis in Diseases of Nerve and Muscle, P A Davis, Philadelphia, 1989.
5. J A Liveson: Peripheral Neurology, F A Davis Company, Philadelphia, 1991.
6. R D Adams and M Victor: Principles of Neurology, McGraw-Hill, New York, 1993.
7. A O Perotto: Anatomic Guide for the Electromyographer: The Limbs and Trunk, C C Thomas, Springfield, Ill, 1994.
8. L P Rowland: Merritt's Textbook of Neurology, Williams and Wilkins, Baltimore, 1995.
9. R J Joynt and R C Griggs: Clinical Neurology, Lippincott Williams and Wilkins, Philadelphia, 1998.

BRIEF SUMMARY OF THE INVENTION

The current practice of nerve-damage localization by EMG is fraught with human drawbacks. The basic idea behind the EMGAssistant program is to implement the human EMGer's practical and logical endeavors in making EMG diagnosis onto a computer program, that is to find the minimum locations (preferably only one) of nerve-damage that best explain the EMG findings, both the normal and the abnormal ones. At times, the diagnosed nerve-damage location explains the EMG finding completely and at times it does not. In the latter, the EMGer has to make a choice that might not explain some of the EMG findings and may even contradict others (normal and/or abnormal ones). The EMGer uses the severity of the EMG findings and the way they aggregate to guide him to the best diagnosis. The EMGer has to ascertain that any other diagnosis, that is any other nerve-damage location, will explain his finding—normal muscles and the severity of the abnormal ones—even less. The EMGAssistant program follows the mental process the human EMGer goes through. The difference is in that the program will take into consideration all the possible nerve-damage combinations—literally thousands of them in some cases—while the human EMGer would not, and, in practicality, could not.

Basically, the elecromyographer (EMGer) performs his routine EMG study, assigns graded levels of pathology to each of the muscles he examined. This data is input into the program. A priori, the program computes all the possible combinations (sets) of nerve-segment damage, translates them to all possible combinations (sets) of corresponding muscle damage. Once the data is input, the program compares the input with all these muscle-sets using statistical fit criteria. Once the muscle-sets that best fit the EMGer's input are found, they are translated to the nerve-sets that theoretically would have produced them. Among the latter, only the nerve-sets that include the minimum number of damaged nerve-segments are retained and output as the best explanation for the EMGer's findings—the diagnosis.

Figure 1:
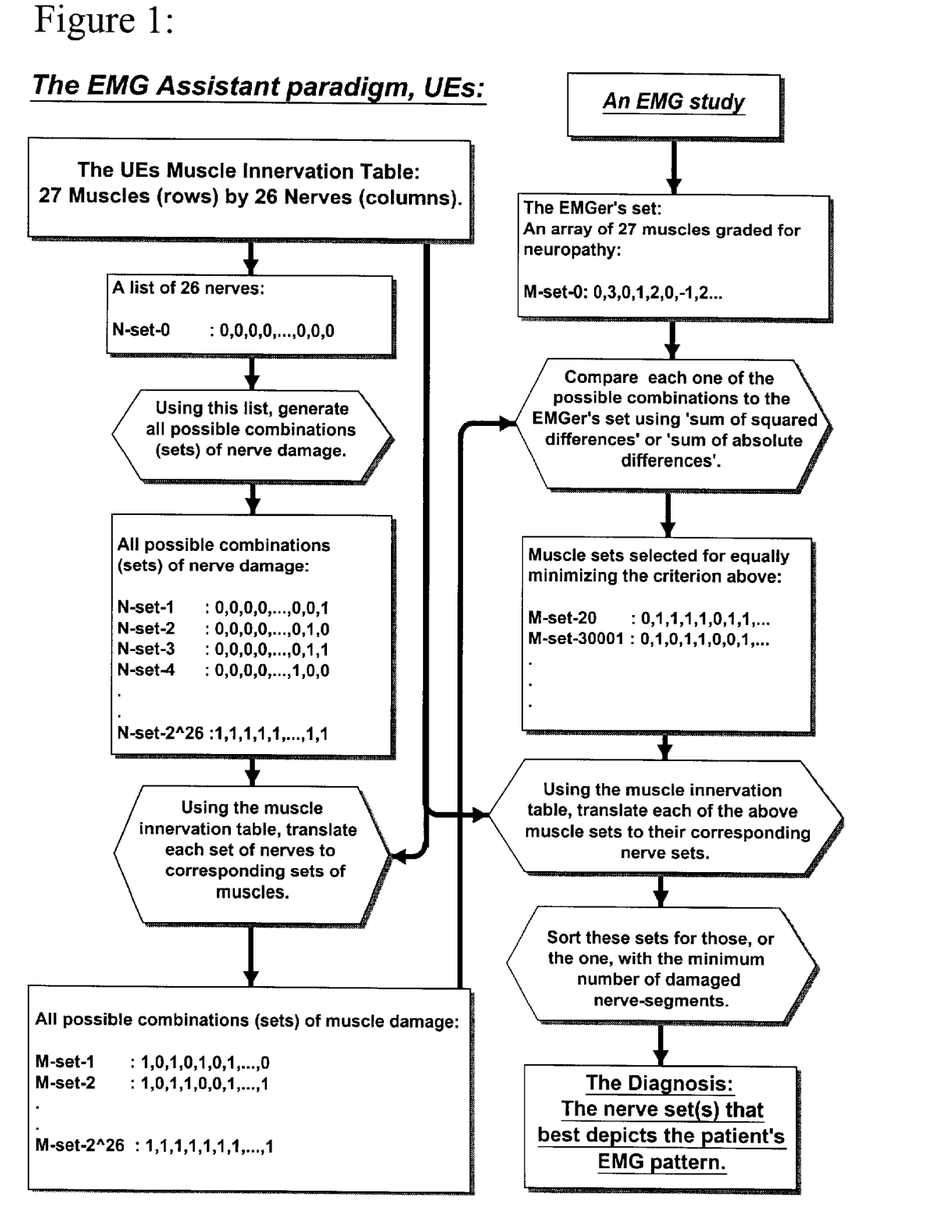
FIG. 1: The EMGAssistant Paradigm, UEs. This flow-chart describes the computer program steps from the moment of its activation (left column), through the input of the electromyographic data (top of right column) on to the computer diagnosis of the damaged nerve-segment(s) (bottom of right column). This flow-chart relates to upper extremities electromyographical examination.
Figure 2:
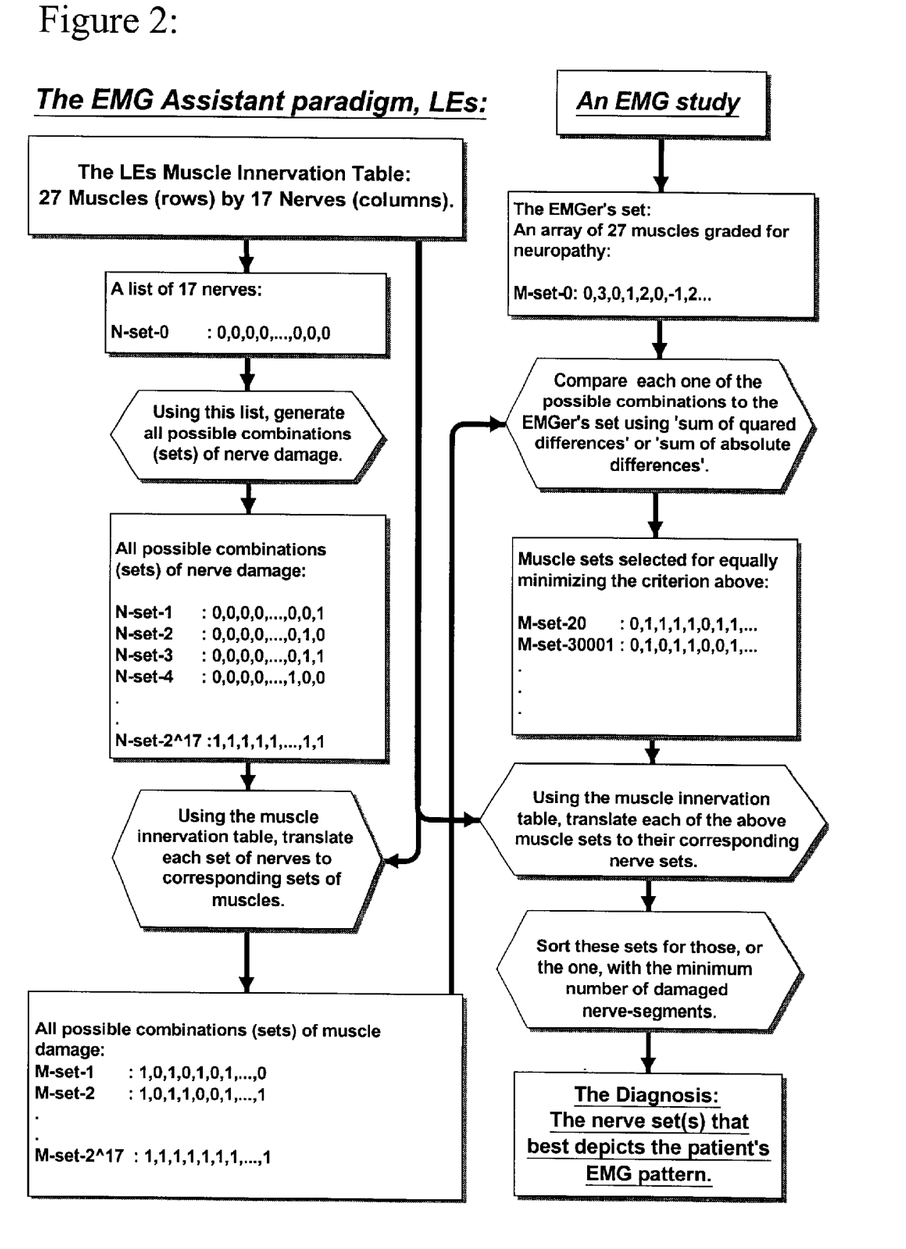
FIG. 2: The EMGAssistant Paradigm, LEs. This flow-chart describes the computer program steps from the moment of its activation (left column), through the input of the electromyographic data (top of right column) on to the computer diagnosis of the damaged nerve-segment(s) (bottom of right column). This flow-chart relates to lower extremities electromyographical examination.

LEGEND TO FIGS. 1 and 2

'0' Normal, for both muscles and nerves.
'1' Abnormal, for both muscles and nerves.
'2' & '3' Additional levels of abnormality, muscles only.
'−1' Muscle not examined.

N-set-0: The sequential array of nerve-segment names as they appear in Tables 1 & 2 (topmost rows) all assigned the value '0' (normal).

N-set-1,2,3 . . . All the possible combinations of nerve-segment damage.

N-set-2^26 This is the last of the upper extremity nerve-segment combinations, the $67,108,864^{th}$ one.

N-set-2^17 This is the last of the lower extremity nerve-segment combinations, the $131,072^{nd}$ one.

M-set-0 The sequential array of muscle names as it appears in Tables 1 & 2 (leftmost columns), each is assigned a value by the Electromyographer.

M-set-20 An example: A muscle-set derived from N-set-20 that best fits M-set-0, i.e., best-fits the electromyographer's findings as determined by the statistical fit criterion.

M-set-30001 An example: A muscle-set derived from N-set-30001 that fits M-set-0 just as well as M-set-20 above.

EMGer Electromyographer

UES, LES Upper extremities and lower extremities.

Note: The values in FIGS. 1 & 2 are only examples. The reader should not compare them with the actual example in the text. Also, the actual program uses shortcuts that are not apparent from FIGS. 1 or 2. These shortcuts are intended to conserve computer memory and accelerate computations.

DETAILED DESCRIPTION OF THE INVENTION

Nerve-to-Muscle Wiring

This Program uses nerve-to-muscle wiring tables, that were adapted from many sources, to translate single and combinations of nerve-segment damage to muscle abnormalities and vice versa (Tables 1, 2). The tables are composed of 27 upper extremities (UES) muscles and 26 corresponding nerve-segments, as well as 27 lower extremities (LES) muscles and 17 corresponding nerve-segments. See *REFERENCES in the 'BACKGROUND OF THE INVENTION' section.

Computational Details

Follow the computational details below and compare with FIGS. 1 and 2.

The Program starts by computing all the hypothetically possible nerve-segment damage/normal-combinations, assigning the value 0 to a normal nerve-segment and the value 1 to a damaged one. This results in $2^{26}=67,108,864$ combinations for the UES, each composed of 26 nerve-segments, and $2^{17}=131,072$ combinations for the LES, each composed of 17 nerve-segments.

For each one of these possible combinations of damaged/normal nerve-segments, the Program generates the theoretically expected muscle-set by using Tables 1 & 2. Within each such muscle-set, the muscles are marked as either neuropathic 1, or normal 0. Below is an example of one (Generated$_n$)of many generated muscle-sets (muscle names were intuitively abbreviated):

|  | Generated$_n$ |
| --- | --- |
| Deltoid | 1 |
| Biceps | 1 |
| Triceps | 0 |
| BR | 0 |
| ECR | 1 |
| Supinator | 1 |
| PT | 1 |

-continued

|  | Generated$_n$ |
| --- | --- |
| FCU | 0 |
| FDP Ulnar | 0 |
| FCR | 0 |
| FDS | 1 |
| FDP Median | 0 |
| FPL | 1 |
| PQ | 1 |
| ECU | 0 |
| EDC | 0 |
| EIP | 0 |
| ADM | 0 |
| FDI | 0 |
| Opponens | 1 |
| APB | 1 |
| Paraspinals High | 0 |
| Paraspinals Low | 0 |
| Serratus Anterior | 0 |
| Infra Spinatus | 0 |
| Supra Spinatus | 1 |
| Rhomboideus | 1 |

In order to use the Program, the electromyographer is required to translate the severity of the needle-EMG findings into numbers in a muscle-set that is identically sequenced as the muscle-sets above. Below is an example of actual EMG data where 0 indicates normal muscle activity, 1, 2, or 3 indicates different levels of muscle neuropathy and −1 indicates muscles that were not tested:

|  | Actual |
| --- | --- |
| Deltoid | 3 |
| Biceps | 3 |
| Triceps | 2 |
| BR | 0 |
| ECR | 0 |
| Supinator | −1 |
| PT | 0 |
| FCU | 2 |
| FDP Ulnar | 2 |
| FCR | 1 |
| FDS | −1 |
| FDP Median | −1 |
| FPL | 2 |
| PQ | −1 |
| ECU | −1 |
| EDC | −1 |
| EIP | 3 |
| ADM | 2 |
| FDI | 1 |
| Opponens | 3 |
| APB | 2 |
| Paraspinals High | −1 |
| Paraspinals Low | 0 |
| Serratus Anterior | −1 |
| Infra Spinatus | 1 |
| Supra Spinatus | 2 |
| Rhomboideus | 1 |

The electromyographer's muscle-set is then compared with each of the computer generated muscle-sets as follows: The Program subtracts each of the computer generated muscle values from the values entered by the electromyographer, one muscle value at a time, following these rules:

1. If both values are positive (1, 2, or 3) or both equal zero the assigned difference is zero.
2. If the electromyographer's value is positive (1, 2, or 3) and the computer value is 0 the assigned difference is the positive value squared (1, 4, or 9).
3. If the electromyographer's value is 0 and the computer value is 1 the assigned difference is NORMVALUE squared. The default value for NORMVALUE is 2. NORMVALUE reflects the electromyographer's confidence in his assessment of the muscle as normal, relative to his assessment of the other muscles as neuropathic.

4. If a muscle was not examined (−1), the computer does not assign the difference a numerical value.

The following is the actual case whose data was given above and that is used as an example to delineate how the EMGAssistant operates:

|  | Acutal | Sequenced Subractions Following the Rules Above | |
|---|---|---|---|
|  |  | Generated$_n$ | Difference |
| Deltoid | 3 | 1 | 0 |
| Biceps | 3 | 1 | 0 |
| Triceps | 2 | 0 | 2 |
| BR | 0 | 0 | 0 |
| ECR | 0 | 1 | 2 |
| Supinator | −1 | 1 |  |
| PT | 0 | 1 | 2 |
| FCU | 2 | 0 | 2 |
| FDP Ulnar | 2 | 0 | 2 |
| FCR | 1 | 0 | 1 |
| FDS | −1 | 1 |  |
| FDP Median | −1 | 0 |  |
| FPL | 2 | 1 | 0 |
| PQ | −1 | 1 |  |
| ECU | −1 | 0 |  |
| EDC | −1 | 0 |  |
| EIP | 3 | 0 | 3 |
| ADM | 2 | 0 | 2 |
| FDI | 1 | 0 | 1 |
| Opponens | 3 | 1 | 0 |
| APB | 2 | 1 | 0 |
| Paraspinals High | −1 | 0 |  |
| Paraspinals Low | 0 | 0 | 0 |
| Serratus Anterior | −1 | 0 |  |
| Infra Spinatus | 1 | 0 | 1 |
| Supra Spinatus | 2 | 1 | 0 |
| Rhomboideus | −1 | 1 |  |

Each value in these arrays of differences is then squared and added to produce the 'sum of the squared differences' as follows.

$$(2)^2+(2)^2+(2)^2+(2)^2+(2)^2+(1)^2+(3)^2+(2)^2+(1)^2+(1)^2=36$$

This measure, the value 36 (above), is a reflection of the difference between the computer generated muscle-set and the electromyographer's entered data. The lower this value is the better is the fit. After computing all the combinations of hypothetical nerve-segment damage, their corresponding muscle-sets and the sums of the squared differences between the latter and the electromyographer's actual input, the program identifies one or more of those muscle-sets that carry the smallest value for the sum of squared differences. As these muscle-sets were computed from known hypothetical damaged/normal nerve-segment combinations, these combinations are identified. From them the program then selects those combinations that have the least number of damaged nerve-segments and reports them as the diagnosis. In the above example, the muscle-set that was selected as best-fitting the electromyographer's actual EMG findings is shown below:

|  | Acutal | Best-fit |
|---|---|---|
| Deltoid | 3 | 3 |
| Biceps | 3 | 3 |
| Triceps | 2 | 2 |
| BR | 0 | 0 |
| ECR | 0 | 0 |
| Supinator | −1 | 0 |
| PT | 0 | 0 |
| FCU | 2 | 2 |
| FDP Ulnar | 2 | 2 |
| FCR | 1 | 1 |
| FDS | −1 | 1 |
| FDP Median | −1 | 1 |
| FPL | 2 | 2 |
| PQ | −1 | 1 |
| ECU | −1 | 1 |
| EDC | −1 | 1 |
| EIP | 3 | 3 |
| ADM | 2 | 2 |
| FDI | 1 | 1 |
| Opponens | 3 | 3 |
| APB | 2 | 2 |
| Paraspinals High | −1 | 0 |
| Paraspinals Low | 0 | 0 |
| Serratus Anterior | −1 | 0 |
| Infra Spinatus | 1 | 1 |
| Supra Spinatus | 2 | 2 |
| Rhomboideus | −1 | 0 |

This specific best fit muscle-set was computed from hypothetically combined lesions of the Musculocutaneous, Axillary, Lower Trunk and Supra Scapular nerves. In this specific case, the latter is the diagnosis.

In addition to identifying the damaged nerve-segment, the program generates two statistics to assess the reliability of the diagnosis (see example of the program output below): A truth table and the Binomial test for the significance of the fit. The truth table summarizes the differences as well as the similarities between the electromyographer's muscle-set and the program chosen best fit muscle-set. It displays the true-positive, true-negative, false-positive and false-negative statistics of this comparison. The Binomial test provides the statistical confidence in the program diagnosis. The smaller the 'p' values are the less likely the diagnosis is incorrect. In the example above, it is highly unlikely that the program diagnosis is incorrect Notes: In this example the range of muscle abnormalities was set from 0 (normal) to 3 (maximally affected), the NORMVALUE criterion was set to 2, the statistical fit criterion was the minimization of the sum of squared differences and each muscle was given equal weight in making the diagnosis. Other abnormality ranges, NORMVALUE values, statistical fit criteria and muscle weights are optional. Using different options will have significant impact on the diagnosis. It is up to the EMGer to choose and use the settings that best suit him.

Computer Program

The method for automated localization of root/plexus/nerve/branch-damage using the routine clinical (needle) electromyographic study results has been implemented into a Microsoft Windows (95, 98, Me, NT, 2000) compatible computer program named the EMGAssistant. This program uses the nerve-to-muscle innervation Tables 1 & 2 and follows FIGS. 1 and 2 with some short cuts to conserve computer memory and improve performance. It is fast and easy to employ.

While the invention is described with reference to a specific embodiment, the description is illustrative of the invention and is not to be construed as limiting the invention. Various modifications and applications may occur to those skilled in the art without departing from the true spirit and scope of the invention as defined by the appended claim. How to use the Emgassistant Program and Some Practical Considerations. Also, An Example of The Program Output The EMGer is expected to do her/his routine EMG studies. It is completely in the EMGer's discretion what muscles to EMG. Then, the EMGer is expected to grade each of the muscles that were EMGed as –1, for muscles that were not done, 0 for muscles that are normal and, 1 or 2 or 3 for different levels of EMG abnormalities. It is completely in the EMGer's discretion how to grade the muscle abnormality. The program will run from the 'Start' button just as any other Windows programs.

Once initiated, the program will ask for the EMGer's report on each of the EMGed muscles, and, when done, will produce an output. This stage can be executed by either the EMGer or a technician, a clerk, etc., as long as they are capable of producing reliable transcripts, and as long as the output shall be inspected and signed by a physician. Automatic diagnosis out of the control of physicians (EMGers) is neither the intent nor the capability of this program.

A few important considerations: The EMGAssistant is intended to localize focal nerve damage in the peripheral nervous system using the (needle) EMG findings. It is not designed, nor is it capable to do this in face of Peripheral Polyneuropathy. Actually, neither human nor machine can. Therefore, if the NCV study, that in my opinion should always precede the EMG, shows signs of Peripheral Polyneuropathy I recommend using the EMGAssistant with caution. Obviously, if the NCV study discloses only Compression Neuropathy the EMGAssistant is expected to add strength to the NCV study by reporting the same, as long as the compression produced neuropathic EMG changes.

The EMGAssistant program has an advantage over the human EMGer, as it will report all possible best answers, the human EMGer usually cannot. Also, if the program finds too many 'best results', it either is the case, or this emanates from testing too few muscles. Usually the human interpreter of the data will not notice it, while the program will. In a way, it is the program indication that the EMGer studied too few muscles, and its subtle advice to the EMGer to sample a few more. It is up to the EMGer to take this advice, or not.

Another issue is of muscles that are known to show neuropathic patterns due to local damage and are of no value, other than causing confusion, in localizing nerve damage. The most notorious in this respect is the Extensor Digitorum Brevis. In my practice I use the Extensor Digitorum Brevis EMG findings only if they are normal or, on the other extreme, if they show abundance of active denervation activities. I suggest others do the same in their practice and when using the EMGAssistant too.

Example of the program output/report (the #s left of the vertical line do not appear in the output).

02/11/00 F1234_ues_right.TXT
(MAXVALUE = ; NORMVALUE = 2; FIT: SUM. SQs )
NUMBER OF DIFFERENT-BUT-EQUAL BEST NERVE-SEGMENT COMBINATIONS = 1

| RESULTS: NERVE DAMAGED | | MUSCLES: | INPUT | BEST FIT |
|---|---|---|---|---|
| 1 Median Wrist | 0 | 1 Deltoid | 3 | 3 |
| 2 Ulnar Wrist | 0 | 2 Biceps | 3 | 3 |
| 3 Radial Supin | 0 | 3 Triceps | 2 | 2 |

-continued

02/11/00 F1234_ues_right.TXT
(MAXVALUE = ; NORMVALUE = 2; FIT: SUM. SQs )
NUMBER OF DIFFERENT-BUT-EQUAL BEST NERVE-SEGMENT COMBINATIONS = 1

| 4 Ant Inteross | 0 | 4 BR | 0 | 0 |
|---|---|---|---|---|
| 5 Median Prona | 0 | 5 ECR | 0 | 0 |
| 6 Ulnar FCU | 0 | 6 Supinator | –1 | 0 |
| 7 Ulnar A Elb | 0 | 7 PT | 0 | 0 |
| 8 Median L Arm | 0 | 8 FCU | 2 | 2 |
| 9 Radian L Arm | 0 | 9 FDP Ulnar | 2 | 2 |
| 10 Radial U Arm | 0 | 10 FCR | 1 | 1 |
| 11 Musc cutan | 1<-- | 11 FDS | –1 | 1 |
| 12 Axillary | 1<-- | 12 FDP Median | –1 | 1 |
| 13 Lat'l Cord | 0 | 13 FPL | 2 | 2 |
| 14 Post'r Cord | 0 | 14 PQ | –1 | 1 |
| 15 Medial Cord | 0 | 15 ECU | –1 | 1 |
| 16 Upper Trunk | 0 | 16 EDC | –1 | 1 |
| 17 Middle Trunk | 0 | 17 EIP | 3 | 3 |
| 18 Lower Trunk | 1<-- | 18 ADM | 2 | 2 |
| 19 T1 Root | 0 | 19 FDI | 1 | 1 |
| 20 C8 Root | 0 | 20 Opponens | 3 | 3 |
| 21 C7 Root | 0 | 21 APB | 2 | 2 |
| 22 C6 Root | 0 | 22 Paraspi High | –1 | 0 |
| 23 C5 Root | 0 | 23 Paraspi low | 0 | 0 |
| 24 L Thoracic | 0 | 24 Serratus Ant | 0 | 0 |
| 25 S Scapular | 1<-- | 25 Inf spinatus | 1 | 1 |
| 26 D Scapular | 0 | 26 Sup spinatus | 2 | 2 |
| | | 27 Rhomboideus | –1 | 0 |

ABNORMAL MUSCLES = 14; #NORMAL MUSCLES = 4; #MUSCLES NOT DONE = 9

| | | INPUT | | |
|---|---|---|---|---|
| STATISITCS: | | Positive | Negative | Total |
| BEST FIT | Positive | True Positive 14 (77.8%) | False Positive 0 ( 0.0%) | 14 ( 77.8%) |
| | Negative | False Negative 0 ( 0.0%) | True Negative 4 (22.2%) | 4 ( 22.2%) |
| | Total | 14 (77.8%) | 4 (22.2%) | 18 (100.0%) |

BINOMIAL TEST, 2-SIDED EXACT PROBABILITIES, p = .0000
ORIGINAL POWER   83        (MAX: 142) | % CORRECT MUSCLES
OF EMG
(")EXPLAINED      83              100.0% | 100.0%
BY BEST-FIT

Legend to the Example of the Program Output/Report Above

Line #1: This line reports the date of the exam, the file name in which this report is saved (in the EMGAssistant directory), the two parameters which are used for defining the data, and the computation fit criterion.

Line #3: In this example, the EMGAssistant makes the diagnosis on the basis of the smallest sum of squared differences and on the smallest number of damaged nerve-segments that can explain the EMGer's findings. However, there might be more than one equally good ("equally best") result (not in the above example). Each equally best set of damaged nerve segment is numbered and printed on sequential pages. A study is more reliable if only one or two of these 'Different-But-Equal Best Nerve Combinations' occur. Having more of the latter usually mean that too few muscles were sampled. In such a case it would be my suggestion to sample more.

Lines #5 to #33: The left column is the most important output of the EMGAssistant. The unaffected nerve-segments are listed with value of '0', while the damaged segments show the value of '1' and arrows pointing toward them (lines 17, 18, 24, 31).

On the right there are 3 columns labeled 'Muscles', 'Input' and 'Best-Fit'. The first is a list of all the muscles and the second show the EMG scores as given by EMGer. The third column, called the 'best-fit' column, shows the theoretically expected list of muscles that ought to occur if the said nerve-segments are to be damaged. In places where the 'input' and the 'best-fit' columns mismatch the best fit ones are surrounded in triangular brackets (not in the above example). Another mismatch is where the muscle was not EMGed (marked −1) but the best fit has a value for it. This is not really a mismatch. One may claim that if that muscle had been EMGed it would have matched. This is also the reason that sampling too few muscles may result in many 'different-but-equal best nerve-segment combinations' (see line #3), as many muscles assume the value of (−1), do not contribute to making the diagnosis and their mismatch as above may be assumed acceptable. This problem is affecting the human analysis and the EMGAssistant analysis of the EMG data equally. However, this type of mismatching is taken into consideration in the statistical section of the EMGAssistant. The human EMGer can not relate to such statistics on his own.

Line #35: This line summarizes the EMGer's raw data.

Lines #37 to #49: This is a 'truth table' showing how the EMGer's and the program best-fit lists match in a two by two table. It shows the true-positive match, that is the number of identical muscles that are abnormal on both the EMGer's and the EMGAssistant best-fit lists. It shows the true-negative match, that is the number of identical muscles that are normal on both lists. It shows the false-positive match, that is the number of identical muscles that on the EMGAssistant best-fit list are abnormal but on the EMGer's list appear as normal. It shows the false-negative match, that is the number of identical muscles that on the EMGAssistant best-fit list are normal but on the EMGer's list appear as abnormal.

It is important to note here, again, that the EMGAssistant looks for best-fit, other choices would have produced more false-positive or/and more false negative scores.

Line #51: The Binomial test measures the significance of the fit between the computer generated best muscle-set and the EMGer's one. It actually estimates the odds that this fit happened by chance. The inference of low likelihood of chance (small values of 'p') is that the chosen combination of the damaged nerve-segments is the most likely diagnosis.

Line #53 and 54: These lines give some additional statistical information to help the EMGer appreciate the strength or weakness of the results. The 'Original Power of the EMG' criterion is the values the EMGer gave the various muscles that where EMGed, squared and totaled (in this example). The criterion 'MAX' is the sum as above but computed with the maximal MAXVALUE allowed, that is it gives the 'Power of the EMG' as if every abnormal muscle was abnormal to the maximum. In both computations the value of normal muscles stays 'NORMVALUE'. Reviewing these two values, in this example 83 and 142, gives the EMGer an estimate of how relatively strong his findings were. Severe, clear-cut pathologies are expected to show the 'Original Power of the EMG' values to be closer to 'MAX'. The criterion 'Original Power of EMG Explained by Best-Fit' on line #54 has three values. The first is the absolute and the second is the percentage portion of the 'Original Power of EMG' explained by the best-fit solution. The third is the percentage of the correct EMG findings explained by the best-fit solution. The latter is actually the summation of the values in cells 1 and 4 (true positive and true negative) in the table above (in the actual example: 77.8%+22.2%=100.0%).

At times, the electromyographer may conclude that the findings are consistent with more than one possible diagnosis, or that the basis for the diagnosis is not solid. In such instances the electromyographer would be right to assume that more muscles are needed to be examined. The same predicament may happen when the program is used. The program consistently provides one of four types of possible outputs:

1. A single diagnosis with significant statistics.
2. A single diagnosis with poor statistics.
3. Multiple diagnoses with significant statistics.
4. Multiple diagnoses with poor statistics.

In the first type a secure diagnosis is provided, and the study is completed. In the second type additional muscles require sampling and the electromyographer has to decide which additional muscles to sample. Notably, in types 3 and 4 the program would advise the electromyographer which additional muscles to examine. This is an additional way the program is useful for the examiner, saves his time and prevents needless sampling of muscles that would not contribute to the diagnosis.

TABLE 1

The Upper Extremities, Nerve-to-Muscle Wiring.

| MUSCLES | Damage location | Median @ Wrist 1 | Ulnar @ Wrist 2 | Radial @ Supinator 3 | Ant. Interosseous 4 | Median @ Pronator 5 | Ulnar @ FCU 6 | Ulnar @ Above 7 | Median @ Low Arm 8 | Radian @ Low Arm 9 | Radial @ Upper 10 | Musc. Cutaneous 11 | Axillary 12 | Lateral Cord 13 |
|---|---|---|---|---|---|---|---|---|---|---|---|---|---|---|
| Deltoid | 1 | | | | | | | | | | | | | x |
| Biceps | 2 | | | | | | | | | | | x | | x |
| Triceps | 3 | | | | | | | | | | x | | | |
| BR | 4 | | | | | | | | x | x | | | | |
| ECR | 5 | | | | | | | | x | x | | | | |
| Supinator | 6 | | | | | | | | x | x | | | | |
| PT | 7 | | | | | | | | x | | | | | x |
| FCU | 8 | | | | | | | x | | | | | | |
| FDP Ulnar | 9 | | | | | | x | x | | | | | | |
| FCR | 10 | | | | x | | | | x | | | | | x |
| FDS | 11 | | | | x | | | | x | | | | | x |
| FDP Median | 12 | | | | X | X | | | X | | | | | x |
| FPL | 13 | | | | X | X | | | X | | | | | x |
| PQ | 14 | | | | X | X | | | X | | | | | x |

TABLE 1-continued

The Upper Extremities, Nerve-to-Muscle Wiring.

| | | | | | | | | | | |
|---|---|---|---|---|---|---|---|---|---|---|
| ECU | 15 | | | X | | | | | x | x |
| EDC | 16 | | | X | | | | | x | x |
| EIP | 17 | | | X | | | | | x | x |
| ADM | 18 | | X | | | | X | X | | |
| FDI | 19 | | X | | | | X | X | | |
| Opponens | 20 | x | | | | x | | x | | |
| APB | 21 | X | | | | X | | | X | |
| Paraspinals High | 22 | | | | | | | | | |
| Paraspinals Low | 23 | | | | | | | | | |
| Serratus Anterior | 24 | | | | | | | | | |
| Infra Spinatus | 25 | | | | | | | | | |
| Supra Spinatus | 26 | | | | | | | | | |
| Rhomboideus | 27 | | | | | | | | | |

| MUSCLES | Damage location | Posterior Cord 14 | Medial Cord 15 | Upper Trunk 16 | Middle Trunk 17 | Lower Trunk 18 | T1 Root 19 | C8 Root 20 | C7 Root 21 | C6 Root 22 | C5 Root 23 | Long Thoracic 24 | Supra Scapcular 25 | Dorsal Scapcular 26 |
|---|---|---|---|---|---|---|---|---|---|---|---|---|---|---|
| Deltoid | 1 | X | | X | | | | | | X | X | | | |
| Biceps | 2 | | | X | | | | | | X | X | | | |
| Triceps | 3 | X | | | X | X | | X | X | | | | | |
| BR | 4 | X | | X | | | | | | X | X | | | |
| ECR | 5 | X | | X | X | | | | | X | X | | | |
| Supinator | 6 | X | | X | X | | | | | X | X | | | |
| PT | 7 | | | X | | | | | X | X | | | | |
| FCU | 8 | | X | | | | X | X | X | | | | | |
| FDP Ulnar | 9 | | X | | | | X | X | X | | | | | |
| FCR | 10 | | X | X | X | X | | | X | X | X | | | |
| FDS | 11 | | X | X | X | X | X | | X | | | | | |
| FDP Median | 12 | | X | | X | X | | | X | X | | | | |
| FPL | 13 | | X | X | X | X | X | X | | | | | | |
| PQ | 14 | | X | | X | X | X | X | X | | | | | |
| ECU | 15 | X | | X | X | X | | X | X | X | | | | |
| EDC | 16 | X | | | X | X | | X | X | | | | | |
| EIP | 17 | X | | | X | X | | X | X | | | | | |
| ADM | 18 | | X | | | X | X | X | | | | | | |
| FDI | 19 | | X | | | X | X | X | | | | | | |
| Opponens | 20 | | X | | | X | X | X | | | | | | |
| APB | 21 | | X | | | X | X | X | | | | | | |
| Paraspinals High | 22 | | | | | | | | | X | X | | | |
| Paraspinals Low | 23 | | | | | | | X | X | | | | | |
| Serratus Anterior | 24 | | | | | | | | | X | X | X | X | |
| Infra Spinatus | 25 | | | X | | | | | | X | X | | X | |
| Supra Spinatus | 26 | | | X | | | | | | X | X | | X | |
| Rhomboideus | 27 | | | | | | | | | | X | | | X |

TABLE 2

The Lower Extremities, Nerve-to-Muscle Wiring.

| MUSCLES | Damage location # | Tibial @ Leg 1 | Peroneal 2 | Peroneal - Deep 3 | Peroneal Above 4 | Gluteal - Inferior 5 | Gluteal - Superior 6 | Sp × VD/ Tibial 7 | SP × DD 8 | LP × VD/ 9 | LP × DD/ Femoral 10 | S2 Root 11 |
|---|---|---|---|---|---|---|---|---|---|---|---|---|
| Paraspinals High | 1 | | | | | | | | | | | |
| Paraspinals Low | 2 | | | | | | | | | | | |
| Gluteus Medius | 3 | | | | | | X | | X | | | |
| Gluteus Maximus | 4 | | | | | X | | | X | | | X |
| Iliopsoas | 5 | | | | | | | | | | X | |

TABLE 2-continued

The Lower Extremities, Nerve-to-Muscle Wiring.

| Muscle | # | C1 | C2 | C3 | C4 | C5 | C6 | C7 | C8 | C9 |
|---|---|---|---|---|---|---|---|---|---|---|
| Vastus Lateralis | 6 | | | | | | | | X | |
| Vastus Medialis | 7 | | | | | | | | X | |
| Adductor Longus | 8 | | | | | | | X | | |
| Gracilis | 9 | | | | | | | X | | |
| TFL | 10 | | | | | X | | X | | |
| Semi Tendinosus | 11 | | | | | | X | | | X |
| Biceps Femoris LH | 12 | | | | | | X | | | X |
| Biceps Femoris SH | 13 | | | | X | | | X | | X |
| TA | 14 | | | X | X | | | X | | |
| PL | 15 | | X | | X | | | X | | |
| PB | 16 | | X | | X | | | X | | |
| Gastrocnemius MH | 17 | X | | | | | | X | | X |
| Gastrocnemius LH | 18 | X | | | | | | X | | X |
| Tibialis Posterior | 19 | X | | | | | | X | | |
| Soleus | 20 | X | | | | | | X | | X |
| FDL | 21 | X | | | | | | X | | X |
| FHL | 22 | X | | | | | | X | | X |
| EDL | 23 | | | X | X | | | X | | |
| EHL | 24 | | | X | X | | | X | | |
| EDB | 25 | | | X | X | | | X | | |
| AH | 26 | X | X | XX | X | | | | | |
| ADM | 27 | X | X | X X | X | | | | | |

| MUSCLES | Damage location # | S1 Root 12 | L5 Root 13 | L4 Root 14 | L3 Root 15 | L2 Root 16 | Tibial @ Foot 17 |
|---|---|---|---|---|---|---|---|
| Paraspinals High | 1 | | X | X | X | | |
| Paraspinals Low | 2 | X | X | | | | |
| Gluteus Medius | 3 | X | X | X | | | |
| Gluteus Maximus | 4 | X | X | | | | |
| Iliopsoas | 5 | | | X | X | X | |
| Vastus Lateralis | 6 | | | X | X | X | |
| Vastus Medialis | 7 | | | X | X | X | |
| Adductor Longus | 8 | | | X | X | X | |
| Gracilis | 9 | | | X | X | X | |
| TFL | 10 | X | X | X | | | |
| Semi Tendinosus | 11 | X | X | | | | |
| Biceps Femoris LH | 12 | X | X | | | | |
| Biceps Femoris SH | 13 | X | X | | | | |
| TA | 14 | | X | X | | | |
| PL | 15 | X | X | | | | |
| PB | 16 | X | X | | | | |
| Gastrocnemius MH | 17 | X | | | | | |
| Gastrocnemius LH | 18 | X | | | | | |
| Tibialis Posterior | 19 | X | X | | | | |
| Soleus | 20 | X | | | | | |
| FDL | 21 | X | X | | | | |
| FHL | 22 | X | X | | | | |
| EDL | 23 | X | X | | | | |
| EHL | 24 | X | X | | | | |
| EDB | 25 | X | X | | | | |
| AH | 26 | X | | | | | X |
| ADM | 27 | X | | | | | X |

Legend to Table 1: The nerve-to-muscle wiring table for the upper extremity is composed of names of nerve-segments in the top row and names of muscles in the left side column. The 'X's inside the table delineates the muscles that are expected to show neuropathic EMG pattern when the corresponding nerve-segment is damaged. The muscle-set includes all the routinely sampled muscles of the upper extremity (muscle and nerve-segment names were intuitively abbreviated). The outlined nerve-segments include all those sites where nerve damage usually occurs.

Legend to Table 2: The nerve-to-muscle wiring table for the lower extremity is composed of names of nerve-segments in the top row and names of muscles in the left side column. The 'X's inside the tables delineates the muscles that are expected to show neuropathic EMG pattern when the corresponding nerve-segment is damaged. The muscle-set includes all the routinely sampled muscles of the lower extremity (muscle and nerve-segment names were intuitively abbreviated). The outlined nerve-segments include all those sites where nerve damage usually occurs. Additional abbreviations:

'SPxVD/Tibial Above Knee': This nerve-segment includes the Tibial nerve above the knee through the Ventral Division of the Sacral Plexus.

'LPxVD/Obturator': This nerve-segment includes the Obturator nerve through the Ventral Division of the Lumbar Plexus.

'LPxDD/Femoral': This nerve-segment includes the Femoral nerve through the Dorsal Division of the Lumbar Plexus.

What I claim as my invention is:

1. A method for automatic localization of nerve damage that can be achieved by electromyography followed by the steps below:

a. Dividing and tabling a peripheral nerve system as a nerve-set composed of multiple, discrete nerve-segments;
b. Computing a different said nerve-set for each one of all possible combinations of normal/abnormal nerve-segments;
c. Computing for each one of said nerve-sets a hypothetical muscle-set of normal/abnormal muscles using a nerve-to-muscle wiring table;
d. Grading electromyographic findings for pathology and recording said findings into a muscle-set that is sequenced identically to said hypothetical muscle-sets in step (c) above;
e. Comparing each one of said hypothetical muscle-sets in (c) above with said graded electromyographic findings, and for each comparison, computing a numerical value for a goodness of fit;
f. Finding said hypothetical muscle-sets that best fit said graded electromyographic findings using said goodness of fit values;
g. Identifying known said nerve-sets in (c) that generated said hypothetical muscle-sets in (f); and
h. Indicating said localization of nerve damage among said identified nerve-sets.

* * * * *